United States Patent [19]

Perlman

[11] Patent Number: 5,098,603

[45] Date of Patent: Mar. 24, 1992

[54] STABILIZED PHENOL SOLUTION

[75] Inventor: Daniel Perlman, Arlington, Mass.

[73] Assignee: Eastman Kodak Company, Rochester, N.Y.

[21] Appl. No.: 465,834

[22] Filed: Jan. 16, 1990

[51] Int. Cl.⁵ .......................... B01F 1/00; C09K 3/30; C07C 39/04
[52] U.S. Cl. .................................... 252/305; 222/519; 222/522; 222/538; 222/571; 252/182.29; 252/182.31; 252/364; 568/716
[58] Field of Search ....................... 252/182.29, 182.31, 252/305, 364; 568/716; 514/731; 222/519, 522, 538, 571

[56] References Cited

U.S. PATENT DOCUMENTS

| | | | |
|---|---|---|---|
| 2,810,499 | 10/1957 | Forman | 222/538 X |
| 2,932,434 | 4/1960 | Abplanalp | 222/394 |
| 3,769,172 | 10/1973 | Bressler et al. | 435/12 |
| 4,102,810 | 7/1978 | Armstrong | 436/16 |
| 4,460,489 | 7/1984 | Kendall | 252/90 |
| 4,892,877 | 1/1990 | Sorrentino | 514/731 X |
| 4,969,577 | 11/1990 | Werding | 222/94 |
| 4,973,551 | 11/1990 | Condra | 435/172.1 X |

OTHER PUBLICATIONS

K. S. Kirby, *Biochemistry Journal*, vol. 64, p. 405 (1956).
K. S. Kirby, *Biochemistry Journal*, vol. 66, p. 495, 501 (1957).
T. Maniatis, et al., J. Sambrook *Molecular Cloning: A Laboratory Manual*, Cold Spring Harbor Publications, (1982).
R. F. Schleif et al., *Practical Methods in Molecular Biology*, pp. 99-100 (1981).
*International Critical Tables*, New York, 1928), pp. 386 and 389.
Taylor et al., "Oxidative Coupling of Phenols", Marcel Dekker, Inc., (New York (1967), pp. 1 and 54-57.
Herzka et al., "Pressurized Packaging (Aerosols)", Second Edition Butterworth & Co., (Publ.) Ltd., London (1961), pp. 84-87 and 102-106.

*Primary Examiner*—Richard D. Lovering
*Attorney, Agent, or Firm*—David M. Woods

[57] ABSTRACT

A buffered and chelated phenol solution has been stabilized by adjusting the pH within a critical range and maintaining the solution under inert gas atmosphere. The solution, which may be combined with chloroform, is useful to denature soluble proteins during the purification of nucleic acids. An opaque phenol-compatible package is described which preserves and safely delivers water-clear phenol.

12 Claims, 1 Drawing Sheet

STABILIZED PHENOL SOLUTION

BACKGROUND OF THE INVENTION

1. Field of the Invention

The present invention is directed to a stabilized phenol or phenol-chloroform solution useful, for example, in the purification of nucleic acids when soluble proteins are to be removed from the nucleic acid solution. The solution remains chemically stable under inert gas atmosphere during long-term storage. The present invention further relates to a phenol compatible package which preserves the chemical stability of the solution and safely delivers the phenol.

2. Description of the Prior Art

The isolation and purification of nucleic acids is basic to all procedures in molecular cloning. For example, when DNA is to be used for genetic engineering, that is, when it is to be cut with restriction enzymes, ligated, kinased, and so on, the DNA needs to be scrupulously clean.

One of the first reports of nucleic acid isolation described the preparation of ribonucleic acid (RNA) from a plant virus (the Tobacco Mosaic Virus) using mild procedures. Viral RNA was successfully separated from nucleoproteins after the proteins had been denatured by heating.

However, early attempts at isolating RNA from mammalian tissues were not entirely satisfactory. Unlike nucleoproteins from tobacco mosaic virus, spontaneous dissociation after heat denaturation did not occur with the mammalian RNA-protein complex. This suggested that the RNA-protein complex obtained from mammals is held by a stronger bond than that from tobacco mosaic virus.

To separate the protein from the RNA, it was essential to denature the proteins by heating the nucleoprotein preparation to 90°-100° C. Since the cell nucleus is the site of genetic material and therefore of DNA, these early methods also involved separation of cell nuclei from the cytoplasm in order to obtain DNA-free cell lysates. This practice, along with other drastic procedures generally used in isolating RNA from mammalian tissues probably caused degradation of RNA. Consequently, early RNA yields were of low molecular weight and were not highly polymerized.

In time, through a lengthy precipitation and ultra centrifugation method it was possible to split off the protein moiety from a glycoprotein by treatment with phenol and water, yielding polysaccharides and RNA's in the aqueous phase. By modifying this method it was also possible to extract mammalian RNA's from nucleoproteins at 68° C. Still further investigations showed that better results could be obtained by performing the extraction at room temperature. (K. S. Kirby, *Biochemistry Journal*, Vol 64, p. 405 (1956)).

In 1956, Kirby devised a method of preparing RNA from mammalian tissues by extraction with phenol and water at room temperature. Kirby found that phenol was essential to the process and concluded that phenol's properties as a protein solvent were important in the separation. The Kirby method had several advantages. Firstly, the deoxyribonucleic acids (DNA's), remained completely insoluble and therefore separable from RNA, thus making it no longer necessary to separate the nuclei before preparing RNA. Secondly, the phenol treatment inactivated ribonucleases in the tissue, and possibly other nucleases as well, thus yielding highly polymerized RNA's.

In 1957, Kirby reported that by modifying his RNA separation technique, he was able to successfully liberate DNA as well. (K. S. Kirby, *Biochemistry Journal*, Vol 66, p. 495, 501 (1957)). By replacing the water in the original phenol-water mixture with solutions of certain anions, DNA as well as RNA was brought into the aqueous layer. It was essential to homogenize the tissue in a salt solution first and then treat with phenol, since no DNA was released by treating tissues with water and phenol and subsequently adding the effective salts. Phenol, acting as a protein solvent, was as essential to the reactions as the salt in solution.

When mammalian tissues are treated with a salt solution and phenol as described above, a DNA-protein complex is liberated. DNA can then be freed completely from protein by using p-aminosalicylate and phenol resulting in a high DNA yield. Also, DNA can be freed completely from RNA by treatment with ribonuclease and precipitation with 2-ethoxyethanol.

The described Kirby method is the basis for current laboratory techniques employed in the separation of RNA and DNA from mammalian tissues. At the present time, when nucleic acids are to be purified from a complex mixture of molecules such as cell lysates, the usual method is to remove most of the protein by digesting with proteolytic enzymes such as pronase or proteinase-K, which are active against a broad spectrum of native proteins. The nucleic acid is subsequently isolated. A key step in the final isolation of nucleic acid is the removal of proteins, a process often carried out by extracting aqueous solutions of nucleic acid with organic solvents such as phenol and/or chloroform.

The removal of proteins from nucleoproteins, the key step of nucleic acid purification, may be carried out by using phenol, but there are two major disadvantages. First, it is crucial to remove from the phenol all contaminants that would bring about cross-linking of RNA and DNA. That is, phenol must be chemically stable and non-reactive with other elements in its environment. Current laboratory manuals describe a lengthy process by which this may be accomplished. (See, for example, T. Maniatis, E. F. Fritsch, J. Sambrook, *Molecular Cloning: A Laboratory Manual*, Cold Spring Harbor Publications, (1982)). However, stabilized phenol solutions must either be prepared as needed or else be stored at 4° C. under equilibration buffer. Under the latter conditions, the solution remains stable only for periods of up to one month.

Second, phenol is highly corrosive and can cause severe burns. It is recommended that safety glasses and gloves be worn while handling phenol. Maniatis, supra, at 438.

In summary, an aqueous phenol solution is regularly used in the purification of nucleic acids, but for this purpose, it must be chemically stable and free of contaminants. Under present laboratory methods, phenol solution becomes unstable shortly after it is prepared. During preparation, extreme caution must be exercised because phenol is highly corrosive.

SUMMARY OF THE INVENTION

The present invention overcomes the disadvantages associated with the prior art by providing a stabilized aqueous phenol solution packaged under stringently purged inert gas atmosphere, comprising:

(a) phenol;

(b) a buffer of about pH 5.0–≦8.0 in an amount sufficient to saturate the phenol; and (c) an ion chelator.

There is also presented a method of preparing the above-described solution.

There is also provided a phenol compatible package for preserving, storing and dispensing said stabilized phenol solution.

BRIEF DESCRIPTION OF THE DRAWINGS

The present invention provides a stabilized phenol solution contained in a phenol compatible package which stores the solution without chemical change and dispenses the solution with minimum risk of physical harm. While the composition and method of the present invention is described with particular reference to an aerosol canister, it will be appreciated that the invention is also useful when a non-aerosol form of packaging is employed. As used herein, the term "aerosol" describes a delivery system wherein a liquid under gas pressure is released preferably in a fluid stream rather than as a spray.

The invention is illustrated, by way of example, in the accompanying schematic drawings wherein.

DETAILED DESCRIPTION OF THE INVENTION

Figures 1, 1A:
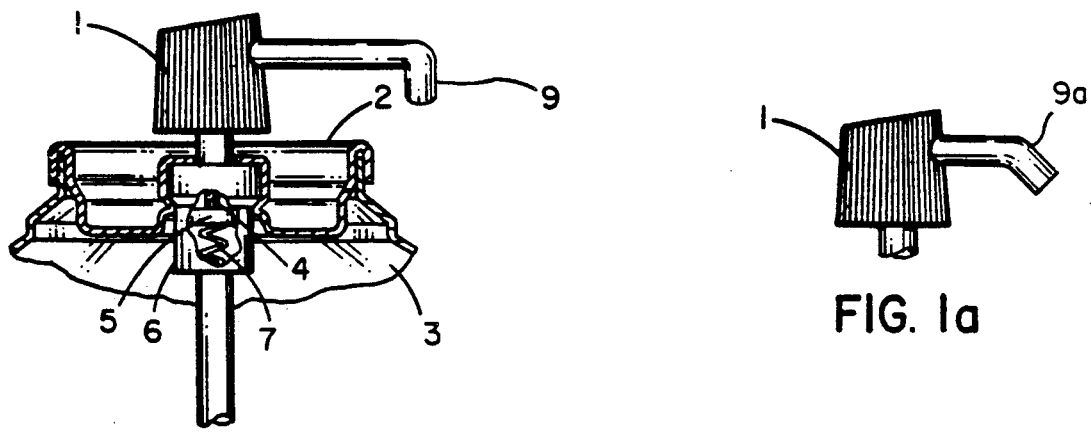
FIG. 1 is a fragmentary view in longitudinal cross-section of the upper portion of a conventional aerosol can showing the basic components of the assembly.
FIG. 1a is an alternative configuration of the elbow extension delivery tube.

The prior art describes the preparation and use of buffered phenol to denature soluble proteins during the purification of nucleic acids. See, for example, Maniatis et al., supra, at pages 438–439 and 458–459; R. F. Schleif and P C. Wensink, *Practical Methods in Molecular Biology* (1981), at pages 99–100. However, such prior art typically suggests Tris-[hydroxymethyl]amino methane (hereinafter Tris) buffer-equilibration of phenol at approximately pH 8.0. See, for example, Maniatis et al., supra, at page 438, line 12; Schleif et al., supra, at page 100, line 14. This suggestion contrasts with and teaches away from the present invention in which the Tris- and/or phosphate-EDTA buffered phenol product is adjusted to a pH below 8.0. The rationale for the present choice of a lower pH range is based on our experience that phenol is more oxidatively reactive at alkaline pH.

Dissociation of the hydroxyl hydrogen of phenol and formation of the more reactive, negatively charged phenoxide ion is favored at alkaline pH. For example, at about pH 8.0, approximately 1% of the phenol is in the form of the phenoxide anion. Therefore, the pH of aqueous buffered phenol is preferably maintained below pH 8.0 but, for reasons discussed below, not lower than about pH 4.5. A slightly acidic pH range (between about pH 5.0 and 7.0) is preferred.

By buffering the phenol solution below about pH 8.0, discoloration of the phenol solution (discoloration is evidence that oxidation has occurred) is retarded and the phenol solution retains the essential water clear appearance even after long term storage. In any case, about pH 5.0 would probably be a lower pH limit (regardless of the pKa of the particular buffer) because the phenol is used to purify solutions which must remain near neutral pH. For example, nucleic acids (DNA and RNA solutions) are the primary solutions being purified. If the phenol were rendered too acidic (less than about pH 4.0) harmful depurination of nucleotides may occur. Thus the preferred pH range for the phenol solution is between about 5.0≦8.0. The useful range is between about 4.5–8.5.

A monobasic-dibasic phosphate buffer system is one example of a chemically unreactive buffer appropriate for maintaining the pH in this range. A solution comprising approximately about 6.8 mM monobasic sodium phosphate and about 3.2 mM dibasic sodium phosphate is useful in establishing a pH of about 6.5.

Freshly distilled phenol is extracted in this buffer until the pH of the aqueous phase remains essentially constant. Phenol is stirred or shaken with the buffer of choice at room temperature, preferably under inert gas atmosphere, until the buffer becomes saturated.

Any chemically stable buffer whose pKa falls within the operative range described above is suitable. Exemplary buffers include acetate, citrate, succinate, piperazine-N, N'-bis(2-ethanesulfonic acid), maleate, phosphate, HEPES (N-2-hydroxyethyl piperazine-N'-2-ethane sulfonic acid), phthalate and cacodylate.

Tris-based buffers, such as 10 mM Tris-phosphate, are also useful in this invention. The buffer concentration is preferably maintained below 100 mM and more preferably between 1 and 20 mM so that the pH of the buffered phenol need not dominate or substantially alter the pH of a sample being phenol-treated.

In accordance with the invention, a divalent ion chelator such as ethylenediamine tetraacetate (EDTA) is also been added to the buffered phenol at between about 0.1 and 10 mM but preferably at a concentration of approximately 1 mM. This chelator serves to remove traces of divalent metal ions, some of which are known to catalyze the oxidation of phenol. We have observed that when even minute traces of metal ions are present, phenol solution is prone to catalytic oxidation, a reaction which is particularly severe at alkaline pH. A minimum but sufficient concentration of EDTA is utilized so as to be an effective chelator without contributing an unnecessary level of this chemical to samples being phenol-treated. For example, DNA samples which are phenol-treated may be subsequently digested with restriction enzymes, many of which would be undesirably inhibited by high levels of EDTA. Ethyleneglycol-bis(-beta-aminoethyl ether) N,N-tetraacetic acid (EGTA) can also be used as the ion chelator.

A mild chemical reducing agent such as sodium thiosulfate or β-mercaptoethanol can be also added to the buffered phenol to further minimize any oxidation-related process which would shorten the lifetime of the phenol solution. The reducing agent selected should be employed in a minimum but sufficient concentration (0.1–10 mM), preferably about 1 mM, so as to avoid establishing an unnecessarily high level of reducing agent in the sample being phenol-treated. Examples of buffered phenol solutions are provided below.

Aqueous phenol is susceptible to light-accelerated air oxidation. Under current methods buffered phenol is freshly prepared and stored only for short periods of time (typically several days), refrigerated in dark bottles, with or without addition of chemical reducing agents. Aqueous buffered phenol is not routinely prepared and stored for long periods of time (months or years). To further extend the lifetime of buffered phenol, the present invention also provides a package with an environment which maintains the chemical stability of the solution.

By packaging the buffered phenol in an opaque container of metal, plastic, or glass, and by nitrogen-purging and nitrogen pressurizing the buffered phenol product, photodecomposition and air oxidation have been essentially eliminated. The present invention preferably utilizes an extra-stringent oxygen removal beyond that suggested by the prior art. Reference is made here to U.S. Pat. No. 2,932,434 (Abplanalp). In accordance with the present invention, the phenol solution and the container are actually fully purged with nitrogen, removing essentially all oxygen (>99%). This process is more thorough than that taught by the prior art cited above which reduces oxygen presence to approximately 10% of the original level, but does not fully eliminate oxygen.

In a preferred embodiment, the container is an aerosol canister of native aluminum which, being opaque to light, eliminates the undesirable effects of photo-oxidation. Native aluminum as used herein refers to uncoated or untreated aluminum. If, however, a polyolefin coating becomes available, such a coating would be acceptable for the purposes of the invention. It should be noted by way of comparison that prior art containers utilize brown glass which only reduce photo-oxidation. Further, as shown in chemical stability tests outlined below (Table II), aluminum provides an unexplained protection against oxidation discoloration of the phenol solutions of the present invention. This protection is evidenced by the long term spectral clarity and absence of color in the solution during storage.

For continued chemical purity of the aerosol buffered phenol product, it is critical that the valve assembly parts be phenol-compatible. In the preferred embodiment the valve assembly components selected are fabricated from materials known to be compatible with phenol. They are:
dip tube—polyethylene or polypropylene
valve spring—stainless steel
stem gasket—viton rubber
valve cup and seal—laminated polypropylene protecting a steel cup
valve actuator—polypropylene
actuator extension tube—polypropylene.

Two critical valve assembly components, the valve stem and the valve body housing which are together responsible for the integrity of the valve, are commercially available only in nylon or acetal plastic. Under normal conditions, nylon dissolves in phenol and acetal (Celcon TM, a copolymer and Delrin TM, a homopolymer), a polyformaldehyde-based polymer plastic, is degraded and weakened by phenol. However, it was empirically discovered that acetal, unlike nylon, maintained chemical and structural integrity when placed in a nitrogen environment with phosphate-buffered phenol.

Contrary to available published commercial information from the DuPont and Celanese Corporations, acetal is surprisingly inert in nitrogen-purged phenol. It appears that the reaction between acetal and phenol might be oxygen mediated. Thus, when the aluminum aerosol canister and the phenol solution are nitrogen-purged in the course of packaging, oxygen is eliminated and the expected phenol-acetal reaction does not take place. As a result, water-clear phenol is obtained under the conditions of the present invention.

FIG. 1 is an illustration of a conventional aerosol can showing the actuator 1 (polypropylene); valve cup 2 (steel protected by laminated polypropylene); canister 3 (native aluminum); valve stem 4 (acetal); stem gasket 5 (viton rubber); valve body housing 6 (acetal); valve spring 7 (stainless steel).

FIG. 1a illustrates an alternate design 9a of the elbow extension delivery tube.

Figure 2:
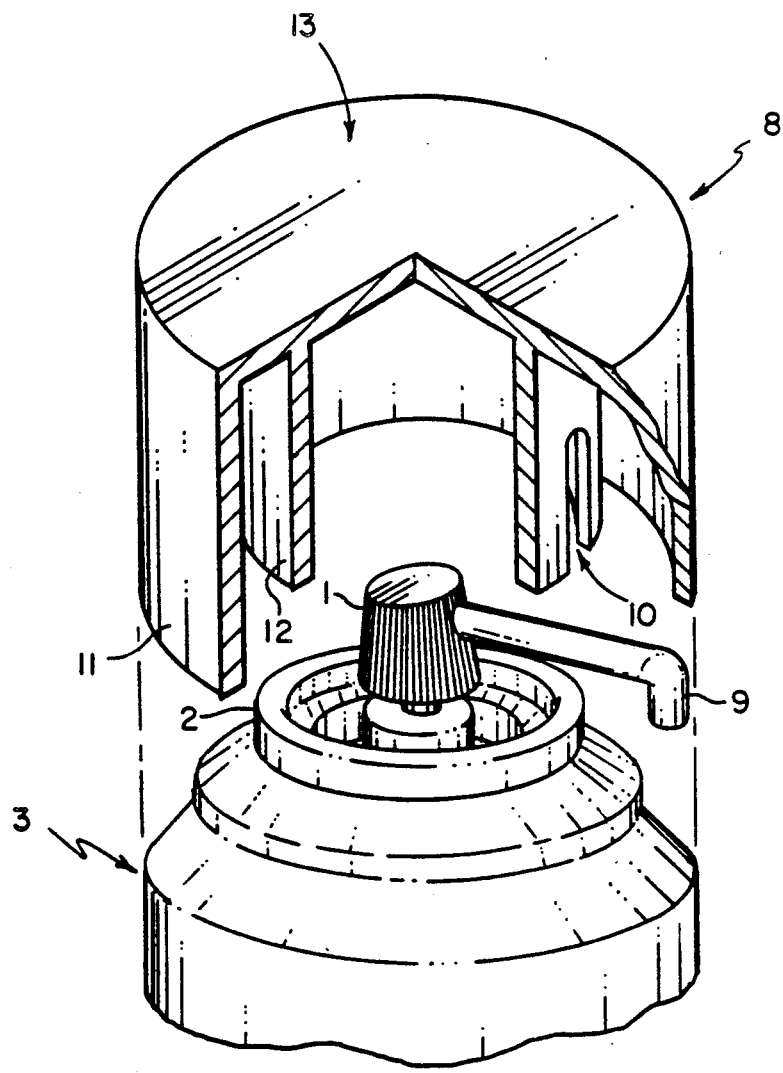
FIG. 2 is a perspective view of the upper portion of the aerosol can of FIG. 1, with the cap 8 removed to show the dispensing extension arm 9 and the groove 10 in the cap 8 which accommodates said extension arm 9.

FIG. 2 illustrates a snap-off cap 8, with an outer skirt 11 and inner skirt 12 depending from the top of the cap 13. An opening 10 in the inner skirt 12 accommodates the short elbow extension delivery tube 9 or 9a which safely and conveniently dispenses the phenol solution. The design of the elbow extension delivery tube 9 allows the solution to be dispensed from the canister into laboratory glassware or plastic ware, such as test tubes or flasks, with minimum risk of spilling the corrosive solution. Inner shirt 12 snaps over shoulder 2 and outer skirt 11 fits on shoulder 3 to enclose elbow extension tube 9 or 9a within cap 8.

DESCRIPTION OF THE PREFERRED EMBODIMENTS

The following examples illustrate the invention but are not to be construed as limiting:

EXAMPLE 1

Buffered Phenol Solution

| | |
|---|---|
| 10 mM | A quantity of Phenol Phosphate Buffer (preferably 6.9 mM monobasic sodium phosphate and 3.1 mM dibasic sodium phosphate) |
| 1 mM | Sodium Thiosulfate |
| 1 mM | EDTA (ethylenediamine tetra-acetic acid) |
| | Distilled Water |
| pH 6.5 | (pH preferably adjusted with sodium hydroxide or phosphoric acid to a final pH of 6.5) |

At room temperature phenol is solid. Solid phenol is put in a standard distillation apparatus and heated at about 180° C. for about 30 minutes.

Vapor from the heated phenol is then condensed in a forced air-cooled condenser to form liquid phenol which is made to drip from the condenser directly into the above-described buffer solution which is prepared before hand and held at room temperature for this purpose. Preferably, the buffer has been nitrogen purged and is held under nitrogen atmosphere preferably in a glass flask.

As the liquid phenol drips into the prepared buffer solution it is shaken or vigorously stirred, preferably with a magnetic glass or TEFLON-coated stirring bar until the phenol becomes saturated with buffer. When the phenol is saturated with buffer, it will be observed that no more buffer enters the phenol.

The denser phenol solution forms a visibly distinct phase at the bottom of the flask and can be easily separated from the less dense phosphate buffer in the upper phase. For best results the saturated phenol solution should be kept under nitrogen and refrigerated at about 4° C. until packaged.

When prepared as described, the solution remains water clear for several months. The respective solutions are prepared as follows:

EXAMPLE 2

Buffer

The method of Example 1 was used except that the composition of the buffer solution is different. The buffer in this example is prepared as follows:

| | | |
|---|---|---|
| 10 mM | Tris (Tris-[hydroxymethyl]amino methane) | |
| 1 mM | EDTA (ethylene diamine tetraacetic acid) | |
| 1 mM | Sodium Thiosulfate | |
| | Distilled Water | |
| pH 6.5 | | |

When prepared as described, the solution remains water-clear for months.

EXAMPLE 3

Buffer

The method of Example 1, was used except that the composition of the buffer solution is different. The buffer in this example is prepared as follows:

| | |
|---|---|
| 10 mM | Tris (Tris-[hydroxymethyl]amino methane) |
| 0.2% | B-Mercaptoethanol |
| 0.1% | 8-Hydroxyquinoline |
| | Distilled Water |
| pH 7.6 | |

When prepared as described, the solution remains water-clear for months.

EXAMPLE 4

Buffer

The method of Example 1, was used except that the composition of the buffer solution is different. The buffer in this example is prepared as follows:

| | |
|---|---|
| 10 mM | Phosphate buffer |
| 1 mM | Sodium Thiosulfate |
| | Distilled Water |
| pH 6.5 | |

EXAMPLE 5

Buffered Phenol Solution with Chloroform

A mixture of Chloroform and isoamyl alcohol (24:1 v/v)

An equal volume of phenol solution (Prepared according to Example 1, 2, 3 or 4 above).

The chloroform and phenol solutions are mixed together. The phenol/chloroform solution remains stable for several months.

EXAMPLE 6

Acetal (Celcon TM) valve stems and bodies, obtained from Seaquist Valves Corporation, were immersed in nitrogen-purged, buffered phenol under nitrogen atmosphere and maintained for five months at room temperature. The valve components were monitored for signs of discoloration and swelling (dimensional change) which would indicate that the acetal value is incompatible with the phenol solution. (−) Denotes no discoloration and less than 1% increase in plastic part dimension.

| RESULTS Stability of Acetal in Nitrogen-Purged Phenol | | | | | |
|---|---|---|---|---|---|
| | Exposure (Months) | | | | |
| | 1 | 2 | 3 | 4 | 5 |
| Discoloration: | — | — | — | — | — |
| | — | — | — | — | — |
| Swelling | — | — | — | — | — |
| | — | — | — | — | — |

These results show that valve components of acetal are chemically compatible with the claimed buffered phenol solution.

EXAMPLE 7

Buffered phenol solutions of 10 mM Tris—1 mM EDTA (pH 6.8) were sealed in 1.5 ml polypropylene vials either in the presence or absence of 1 $cm^2$ squares of aluminum foil (Reynolds). The 1 ml solutions were incubated at room temperature and the vials were exposed to normal fluorescent room lighting. Air (approximately 0.5 ml volume) which was originally present upon sealing the vials, remained in the vials during the course of the experiment. (−) denotes no change (+) denotes slight discoloration (++) denotes moderate discoloration and (+++) denotes deep discoloration.

It should be noted that the solutions in this example were neither nitrogen purged nor held under inert gas. Also, they were exposed to light. Even so, the results show that aluminum had a stabilizing effect on the solution.

| RESULTS Aluminum Stabilization of Buffered Phenol+ | | | | | |
|---|---|---|---|---|---|
| | Exposure (Months) | | | | |
| | 1 | 2 | 3 | 4 | 5 |
| Discoloration: | | | | | |
| With aluminum | — | — | — | — | −/+ |
| Without aluminum | −/+ | + | ++ | +++ | +++ |

Discoloration is a sign that oxidation has occurred. These results indicate that little or no oxidation occurred when aluminum contacted the phenol solution. Thus, aluminum appears to have a stabilizing effect on the buffered phenol.

The invention has been described in detail with particular reference to preferred embodiments thereof, but it will be understood that variations and modifications can be effected within the spirit and scope of the invention.

I claim:

1. A stabilized phenol solution, comprising:
   (a) phenol;
   (b) a buffer of about pH 5.0–≦7.6 in an amount sufficient to saturate the phenol; and
   (c) an ion chelator.

2. A solution comprising the phenol solution of claim 1 and chloroform.

3. The solution of claims 1 or 2, wherein the pH is between about 5.0 and ≦7.0.

4. A method of maintaining the chemical stability of a saturated phenol solution, comprising:

(a) adjusting the pH of the saturated phenol solution to a value of about 5.0–≦7.6;
(b) adding a chelating agent; and
(c) purging the phenol solution with an inert gas.

5. The method of claim 4, wherein the pH of the phenol solution is adjusted to about 5.0–≦7.0.

6. The method recited in claim 4, wherein the chemical stability of said saturated phenol solution is further improved by maintaining contact between the saturated phenol solution and a surface of native aluminum.

7. The method recited in claims 4 or 6 wherein the chemical stability of said saturated phenol solution is further improved by adding a reducing agent.

8. A container for maintaining the chemical stability of a buffered saturated phenol solution in an inert gas atmosphere comprising:
   a quantity of buffered saturated phenol solution having a pH value of about 5.0 to ≦7.6;
   wall means for confining and protecting said solution, said wall being opaque to light, chemically unreactive to phenol and having a discharge outlet through which the phenol solution can be dispensed;
   delivery and valve means of said outlet controlling the flow of said phenol solution through said outlet, wherein one or more portions of said valve means that contacts said solution comprises a material of acetal.

9. The container recited in claim 8 and further including an elbow extension delivery tube mounted and leading downward from an actuator button located on said valve means of said discharge outlet.

10. The container recited in claim 9 wherein said extension tube is accommodated within a cap positioned over the delivery and valve means of said container.

11. The container of claim 8, wherein the inner surface of said wall means comprises native aluminum.

12. A container for maintaining the stability of a buffered saturated phenol solution in an inert gas atmosphere, comprising:
   A quantity of buffered saturated phenol solution having a pH value of about 7.0 to ≦7.6 in said container;
   wall means, non-reactive with phenol, for confining said solution;
   and further including within said wall means a surface of native aluminum in contact with said phenol solution.

* * * * *

UNITED STATES PATENT AND TRADEMARK OFFICE
CERTIFICATE OF CORRECTION

PATENT NO. : 5,098,603
DATED : March 24, 1992
INVENTOR(S) : Daniel Perlman

It is certified that error appears in the above-identified patent and that said Letters Patent is hereby corrected as shown below:

On the title page, item [73], delete "Eastman Kodak Company, Rochester, N.Y.", and insert --Brandeis University, Waltham, Massachusetts--;

and

Attorney, Agent, or Firm, delete "David M. Woods" and insert --Doreen M. Wells--.

Signed and Sealed this

Seventh Day of September, 1999

Attest:

Q. TODD DICKINSON

Attesting Officer     Acting Commissioner of Patents and Trademarks